(12) United States Patent
Fleys et al.

(10) Patent No.: US 9,096,479 B2
(45) Date of Patent: Aug. 4, 2015

(54) PROCESS FOR PREPARING A PARAFFIN PRODUCT

(71) Applicant: SHELL OIL COMPANY, Houston, TX (US)

(72) Inventors: Matthieu Simon Henri Fleys, Amsterdam (NL); Tathagata Goswami, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/369,468

(22) PCT Filed: Dec. 28, 2012

(86) PCT No.: PCT/EP2012/077094
§ 371 (c)(1),
(2) Date: Jun. 27, 2014

(87) PCT Pub. No.: WO2013/098412
PCT Pub. Date: Jul. 4, 2013

(65) Prior Publication Data
US 2015/0011663 A1    Jan. 8, 2015

(30) Foreign Application Priority Data

Dec. 30, 2011 (EP) .................................... 11196229

(51) Int. Cl.
| | |
|---|---|
| C07C 27/06 | (2006.01) |
| C07C 5/03 | (2006.01) |
| C01B 3/02 | (2006.01) |
| C01B 3/12 | (2006.01) |
| C01B 3/36 | (2006.01) |
| C07C 1/04 | (2006.01) |

(52) U.S. Cl.
CPC ... *C07C 5/03* (2013.01); *C01B 3/02* (2013.01); *C01B 3/12* (2013.01); *C01B 3/36* (2013.01); *C07C 1/0485* (2013.01); *C01B 2203/025* (2013.01); *C01B 2203/0283* (2013.01); *C01B 2203/047* (2013.01); *C01B 2203/062* (2013.01); *C01B 2203/1076* (2013.01); *C07C 2523/06* (2013.01); *C07C 2523/72* (2013.01)

(58) Field of Classification Search
None
See application file for complete search history.

(56) References Cited

U.S. PATENT DOCUMENTS

| | | | |
|---|---|---|---|
| 4,350,103 | A | 9/1982 | Poll |
| 4,458,607 | A | 7/1984 | Schoeber et al. |
| 2006/0076272 | A1 | 4/2006 | Stil |
| 2008/0234397 | A1 | 9/2008 | Gimpel et al. |

FOREIGN PATENT DOCUMENTS

| | | |
|---|---|---|
| EP | 1860063 A1 | 11/2007 |
| GB | 1050873 A | 12/1966 |
| WO | 9603345 A1 | 2/1996 |
| WO | 02070629 A1 | 9/2002 |
| WO | 03035590 A1 | 5/2003 |
| WO | 03035591 A | 5/2003 |
| WO | 2007068682 A1 | 6/2007 |
| WO | 2008006787 A2 | 1/2008 |

OTHER PUBLICATIONS

PCT International Search Report, Application No. PCT/EP2012/077094 dated Mar. 26, 2013.

*Primary Examiner* — Sudhakar Katakam

(57) ABSTRACT

The invention relates to a process for preparing a paraffin product from a carbonaceous feedstock comprising (a) partial oxidation of the carbonaceous feedstock to obtain a mixture comprising hydrogen and carbon monoxide, (b) performing a Fischer-Tropsch reaction using the mixture as obtained in step (a) and recovering an off-gas from the Fischer-Tropsch reaction and a paraffin product, (c) hydrogenating at least a part of the off-gas from the Fischer-Tropsch reaction using a steam/off-gas mol ratio in the range of between 0.5 and 1.5 and a catalyst comprising copper and zinc, followed by a conversion step (d) using a nickel based catalyst, and (e) preparing a hydrogen comprising gas from at least a part of the off-gas from the Fischer-Tropsch reaction.

11 Claims, No Drawings

PROCESS FOR PREPARING A PARAFFIN PRODUCT

CROSS-REFERENCE TO RELATED APPLICATIONS

The present application is a National Stage (§371) of International Application No. PCT/EP2012/077094, filed Dec. 28, 2012, which claims priority from European Application No. EP 11196229.6, filed Dec. 30, 2011, the disclosures of each of which are hereby incorporated by reference in their entirety.

The invention is directed to a process for preparing a paraffin product from a carbonaceous feedstock comprising the following steps, (a) partial oxidation of the carbonaceous feedstock to obtain a mixture comprising hydrogen and carbon monoxide, (b) performing a Fischer-Tropsch reaction using the mixture as obtained in step (a) and recovering an off-gas from the Fischer-Tropsch reaction.

Such a process is described in WO-A-03/035590 and in WO-A-03/035591. In these publications it is described to recirculate the off-gas, referred to therein as tail gas, back into the Fischer-Tropsch reactor of step (b) or into gasifiers of step (a). Gasifiers produce CO and $H_2$ for onward reaction in the Fischer-Tropsch reaction. The off-gas will comprise according to one of these publications water, $CO_2$, $CH_4$, $N_2$, unreacted syngas ($H_2$ and CO) and vapour hydrocarbon products.

Whilst some of the off-gas can be recirculated to the Fischer-Tropsch reactor, recirculation of all of the off-gas to the Fischer-Tropsch reactor causes $CO_2$, $CH_4$ and inerts to build up thus reducing the amount of hydrocarbons produced by the Fischer-Tropsch reactor. This is the case whether coal, biomass or natural gas is used as carbonaceous feedstock.

Feeding the off-gas back to the gasifiers (which produce the $H_2$ and CO mixture) results in problems relating to the relative ratio of $H_2/CO$. For example, coal gasifiers typically produce a $H_2/CO$ ratio which is lower than the preferred ratio to perform step (b). Recirculation of off-gas to the gasifiers will even further reduce this ratio. In case natural gas is gasified, feeding the off-gas back to the gasifiers (which produce the $H_2$ and CO mixture) will also results in problems relating to the relative ratio of $H_2/CO$.

The third option disclosed in WO03/035590 is to use the off-gas as a fuel for power generation. However, in practice this may not consume all of the available off-gas.

Processes in which the off-gas is used in a more efficient manner have been described in US2008023497A1 and in EP1860063.

In one method described in US2008023497A1 and in EP1860063, Fischer-Tropsch off-gas is hydrogenated in a first reactor and subjected to a shift reaction in a second reactor. The resulting Fischer-Tropsch off-gas, with reduced olefin content and reduced carbon monoxide content, is fed into a steam reformer.

In the first reactor unsaturated hydrocarbons are hydrogenated. US2008023497A1 teaches that copper/zinc oxide catalysts are suitable catalysts for the olefin hydrogenation. EP1860063 lists copper/zinc oxide, nickel, nickel/tungsten, cobalt/molybdenum and sulfided nickel/molybdenum catalysts as suitable catalysts for the olefin hydrogenation, with a preference for copper/zinc oxide catalysts, more preferably copper/zinc oxide catalysts to which manganese has been added.

In the second reactor carbon monoxide is removed via a shift reaction with water. This reaction results in carbon dioxide and hydrogen. US2008023497A1 teaches that iron/chromium catalysts are suitable catalysts for the shift reaction. EP1860063 lists iron/chromium, copper/zinc oxide and nickel/cobalt as suitable catalysts for the shift reaction.

In another method described in US2008023497A1 and in EP1860063, Fischer-Tropsch off-gas is subjected to hydrogenation using a pre-reforming catalyst which also promotes methanation of carbon monoxide. In this case olefin hydrogenation and carbon monoxide removal take place simultaneously and in one reactor. US2008023497A1 lists nickel/Al2O3 catalysts, iron, cobalt, NiMo, TiW, platinum, ruthenium and rhenium catalysts as suitable pre-reforming catalysts. EP1860063 lists platinum, ruthenium and rhenium catalysts, and nickel based catalysts, for example nickel on alumina, as suitable pre-reforming catalysts.

The present invention relates to an optimised process. Especially the process of hydrogenating the off-gas from the Fischer-Tropsch reactor has been optimised so that a very stable catalyst performance is achieved. This is advantageous because optimal process conditions can now be maintained for the entire catalyst life time of the hydrogenation catalyst, and the catalyst life time has been increased significantly.

The present invention relates to a process for preparing a paraffin product from a carbonaceous feedstock comprising the following steps:
(a) partial oxidation of the carbonaceous feedstock to obtain a mixture comprising hydrogen and carbon monoxide,
(b) performing a Fischer-Tropsch reaction using the mixture as obtained in step (a) and recovering an off-gas from the Fischer-Tropsch reaction and a paraffin product,
(c) subjecting at least a part of the off-gas from the Fischer-Tropsch reaction to hydrogenation using a steam/off-gas mol ratio in the range of between 0.5 and 1.5, preferably between 0.7 and 1.5, and a catalyst comprising copper and zinc or a catalyst comprising copper, zinc and manganese,
(d) subjecting at least a part of the gas resulting from step (c) to conversion using a nickel based catalyst which comprises at most 0.2 wt % cobalt, at most 0.2 wt % iron and at most 0.2 wt % ruthenium, calculated on the total weight of the catalyst, and
(e) preparing a hydrogen comprising gas from at least a part of the gas resulting from step (d), preferably using a reforming process, more preferably using a steam reforming process, even more preferably using a steam methane reforming process, an adiabatic steam reforming process, a fired steam reforming process, or an auto thermal steam reforming process, most preferably using an adiabatic steam reforming process or a steam methane reforming process.

Preferably all steps of the process of the invention are performed in the order of numbering. The process may comprise additional steps.

Applicants found that by performing step (e) the off-gas may find use as feedstock to prepare a hydrogen comprising gas product. This is advantageous because in the process to be improved by the present invention additional hydrogen is required in order to either optimise the hydrogen to CO ratio of the syngas obtained in step (a) and/or to further upgrade the products as obtained in step (b) by one or more hydroprocessing steps.

Additionally, applicants found that the relatively high steam/off-gas mol ratio used in step (c) results in increased carbon monoxide consumption next to the hydrogenation of olefins and/or paraffins of step (c).

Further, less oxygenates are formed in step (c) as compared to a hydrogenation process in which a lower steam/off-gas mol ratio is used. This is advantageous as oxygenates may stick to the active sites of the copper/zinc hydrogenation catalyst and thereby reduce its activity. This is also advantageous as oxygenates may be converted into olefins when contacted with the nickel based catalyst of step (d), which olefins can cause gum formation and result in a reduced activity of the nickel based catalyst.

Furthermore, applicants found that this optimised procedure results in a very stable catalyst performance for the hydrogenation catalyst of step (c) which comprises copper and zinc and optionally manganese. This is advantageous because optimal process conditions can now be maintained for the entire catalyst life time of the hydrogenating catalyst, and the catalyst life time has been increased significantly.

Additionally, applicants found that the conversion of step (d) can be performed in an optimal way as the feed to step (d) comprises hardly any oxygenates. Furthermore, in step (d) most of the carbon monoxide that was not converted yet in step (c) will be converted in step (d). This way a gas is obtained that has an acceptable carbon monoxide content when it is used in step (e). When step (e) concerns a reforming process, for example an adiabatic steam reforming process or a steam methane reforming process, the remaining low carbon monoxide level in the gas resulting from step (d) that is fed to step (e) will not cause any problems.

Step (a)

In step (a) a carbonaceous feedstock is partially oxidized with an oxygen comprising gas. This is also referred to as gasification. The carbonaceous feedstock may be coal, biomass or natural gas.

The gasification in step (a) may be carried out by partially oxidating natural gas. The gasification in step (a) may be carried out by partially oxidating natural gas according to the shell gasification process (SGP) by partial oxidation of natural gas using pure oxygen.

Partial oxidation of natural gas using pure oxygen may be operated at 1100 to 1700° C. Preferably partial oxidation of natural gas using pure oxygen is operated at 1300 to 1500° C. and pressures up to 70 bar. Another example of a process for partially oxidating natural gas is described in WO9603345A1 where a mixture of carbon monoxide and hydrogen is prepared by partial oxidation of natural gas in a co-annular burner using 99.5% pure oxygen and optionally carbon dioxide as moderator gas and in the absence of a catalyst. A further example is described in WO2008006787A2. In the process of WO2008006787A2 partial oxidation on a methane comprising feed is performed using a multi-orifice burner provided with an arrangement of separate passages, wherein the gaseous hydrocarbon having at elevated temperature flows through a passage of the burner, an oxidiser gas flows through a separate passage of the burner and wherein the passage for gaseous hydrocarbon feed and the passage for oxidiser gas are separated by a passage through which a secondary gas flows, wherein the secondary gas comprises hydrogen, carbon monoxide and/or a hydrocarbon.

The gasification in step (a) may be carried out by partially combusting coal with a limited volume of oxygen at a temperature normally between 800° C. and 2000° C. in the absence of a catalyst. If a temperature of between 1050 and 2000° C. is employed, the product gas will contain very small amounts of gaseous side products such as condensable tars, phenols and hydrocarbons. Suitable coals include lignite, bituminous coal, sub-bituminous coal, anthracite coal, and brown coal. Lignites and bituminous coals are preferred. In order to achieve a more rapid and complete gasification, initial pulverisation of the coal is preferred. Particle size is preferably selected so that 70% of the solid coal feed can pass a 200 mesh sieve. The gasification is preferably carried out in the presence of oxygen and steam, the purity of the oxygen preferably being at least 90% by volume, nitrogen, carbon dioxide and argon being permissible as impurities. Substantially pure oxygen is preferred, such as prepared by an air separation unit (ASU). If the water content of the coal is too high, the coal is preferably dried before use. The atmosphere will be maintained reducing by the regulation of the weight ratio of the oxygen to moisture and ash free coal in the range of 0.6 to 11, preferably 0.8 to 1.0. For example, the procedures described in US4350103 and US4458607 may be employed. Although, in general, it is preferred that the ratio between oxygen and steam be selected so that from 0 to 0.3 parts by volume of steam is present in the reaction one per part by volume of oxygen, the invention is applicable to processes having substantially different ratios of oxygen to steam. The oxygen used is preferably heated before being contacted with the coal, preferably to a temperature of from about 200 to 500° C. Step (a) is preferably performed by partial oxidation of a dry mixture of coal particles and a carrier gas with oxygen in a membrane walled gasification reactor. Membrane wall reactors are known and for example described in US20060076272A1. Preferably the hot mixture of hydrogen and carbon monoxide as obtained in the gasification reactor is cooled by direct contacting the hot gas with liquid water, also referred to as a water quench.

For coal-derived syngas the $H_2/CO$ ratio of the gas mixture obtained in step (a) generally about or less than 1, and is commonly about 0.3-0.6. Such a ratio is suited for an iron catalyzed Fischer-Tropsch reaction. Because the low temperature cobalt catalysed Fischer-Tropsch reaction has a higher consumption ratio of between 2.0 and 2.1, additional hydrogen is needed. By conversion of part of the carbon monoxide as present in the gas mixture obtained in step (a) by means of the water gas shift reaction an increased amount of hydrogen is obtained thereby adjusting the $H_2/CO$ ratio of the gas mixture to a value more suited for performing step (b). A part of the hydrogen as prepared in step (e) may also be advantageously be used to modify the $H_2/CO$ ratio of the gas mixture, thereby requiring less of the water gas shift reaction.

The catalytic water shift conversion reaction provides a hydrogen enriched, often highly enriched, syngas, possibly having a $H_2/CO$ ratio above 3, more suitably above 5, preferably above 7, more preferably above 15, possibly 20 or even above. The water shift conversion reaction is well known in the art and is for example described in the earlier referred to WO03035591A1. Generally, water, usually in the form of steam, is mixed with the syngas to form carbon dioxide and hydrogen. The catalyst used can be any of the known catalysts for such a reaction, including iron, chromium, copper and zinc. Copper on zinc oxide is a known shift catalyst. A very suitable source for the water required in the shift reaction is the product water produced in the Fischer-Tropsch reaction. Preferably this is the main source, e.g. at least 80% is derived from the Fischer-Tropsch process, preferably at least 90%, more preferably 100%. Thus the need of an external water source is minimised. Another preferred source of water is the quench water used to cool the hot gas in step (a) as described above.

When the gas mixture obtained in step (a) is coal-derived syngas, the desired ratio of hydrogen and carbon monoxide of the gas mixture to be used in step (b) is preferably controlled by passing only part of the gas obtained in step (a) over the catalytic water shift reaction as described above. In this manner one can target the desired ratio in an efficient manner, independent of the quality, that is the proportions of carbon and hydrogen, of the solid carbonaceous feedstock.

Especially when the gas mixture obtained in step (a) is coal-derived syngas, the mixture of hydrogen and carbon monoxide of step (a) may be passed through a carbon dioxide/hydrogen sulfide ($CO_2/H_2S$) removal system. This may also be performed when the gas mixture obtained in step (a) is natural gas-derived syngas. The removal system may involve one or more removal units. The $CO_2/H_2S$ removal system preferably uses a physical solvent process, especially methanol or sulfolan, preferably methanol. This process is based on carbon dioxide and hydrogen sulfide being highly soluble under pressure in the solvent, and then being readily releasable from solution when the pressure is reduced as further discussed below. This high pressure system is preferred due to its efficiency, although other removal systems such as using amines are known.

It is preferred to remove at least 80 vol %, preferably at least 90 vol %, more preferably at least 95 vol % and at most 99.5 vol %, of the carbon dioxide present in the optionally catalytically shifted syngas stream. This avoids the build-up of inerts in the Fischer-Tropsch process.

On an industrial scale there are chiefly two categories of absorbent solvents, depending on the mechanism to absorb the acidic components: chemical solvents and physical solvents. Each solvent has its own advantages and disadvantages as to features as loading capacity, kinetics, regenerability, selectivity, stability, corrosivity, heat/cooling requirements etc.

Chemical solvents which have proved to be industrially useful are primary, secondary and/or tertiary amines derived alkanolamines. The most frequently used amines are derived from ethanolamine, especially monoethanol amine (MEA), diethanolamine (DEA), triethanolamine (TEA), diisopropanolamine (DIPA) and methyldiethanolamine (MDEA).

Physical solvents which have proved to be industrially suitable are cyclo-tetramethylenesulfone and its derivatives, aliphatic acid amides, N-methylpyrrolidone, N-alkylated pyrrolidones and the corresponding piperidones, methanol, ethanol and mixtures of dialkylethers of polyethylene glycols.

A well-known commercial process uses an aqueous mixture of a chemical solvent, especially DIPA and/or MDEA, and a physical solvent, especially cyclotetramethylene-sulfone. Such systems show good absorption capacity and good selectivity against moderate investment costs and operational costs. They perform very well at high pressures, especially between 20 and 90 bara.

The physical adsorption process useable in the present invention is well known to the man skilled in the art. Reference can be made to e.g. Perry, Chemical Engineerings' Handbook, Chapter 14, Gas Absorption. The absorption process useable in the present process is a physical process. Suitable solvents are well known to the man skilled in the art and are described in the literature. In the present process the liquid absorbent in the physical absorption process is suitably methanol, ethanol, acetone, dimethyl ether, methyl i-propyl ether, polyethylene glycol or xylene, preferably methanol. The physical absorption process is suitably carried out at low temperatures, preferably between $-60°$ C. and $0°$ C., preferably between $-30$ and $-10°$ C.

The physical absorption process is carried out by contacting the light products stream in a counter-current upward flow with the liquid absorbent. The absorption process is preferably carried out in a continuous mode, in which the liquid absorbent is regenerated. This regeneration process is well known to the man skilled in the art. The loaded liquid absorbent is suitably regenerated by pressure release (e.g. a flashing operation) and/or temperature increase (e.g. a distillation process). The regeneration is suitably carried out in two or more steps, preferably 3-10 steps, especially a combination of one or more flashing steps and a distillation step.

The regeneration of solvent from the process is also known in the art. Preferably, the present invention involves one integrated solvent regeneration tower.

The gas mixture of step (a) may also be passed over additional removal systems, guards or scrubbing units, either as back-up or support to the $CO_2/H_2S$ removal system, or to assist in the reduction and/or removal of other contaminants such as HCN, $NH_3$, COS and $H_2S$, metals, carbonyls, hydrides or other trace contaminants.

Step (b)

The Fischer-Tropsch synthesis of step (b) is well known to those skilled in the art and involves synthesis of hydrocarbons from a gaseous mixture of hydrogen and carbon monoxide, by contacting that mixture at reaction conditions with a Fischer-Tropsch catalyst.

Products of the Fischer-Tropsch synthesis may range from methane to heavy paraffinic waxes. Preferably, the production of methane is minimised and a substantial portion of the hydrocarbons produced have a carbon chain length of a least 5 carbon atoms. Preferably, the amount of $C_5+$ hydrocarbons is at least 60% by weight of the total product, more preferably, at least 70% by weight, even more preferably, at least 80% by weight, most preferably at least 85% by weight.

Fischer-Tropsch catalysts are known in the art, and typically include a Group VIII metal component, preferably cobalt, iron and/or ruthenium, more preferably cobalt. Typically, the catalysts comprise a catalyst carrier. The catalyst carrier is preferably porous, such as a porous inorganic refractory oxide, more preferably alumina, silica, titania, zirconia or mixtures thereof.

The optimum amount of catalytically active metal present on the carrier depends inter alia on the specific catalytically active metal. Typically, the amount of cobalt present in the catalyst may range from 1 to 100 parts by weight per 100 parts by weight of carrier material, preferably from 10 to 50 parts by weight per 100 parts by weight of carrier material.

The catalytically active metal may be present in the catalyst together with one or more metal promoters or co-catalysts. The promoters may be present as metals or as the metal oxide, depending upon the particular promoter concerned. Suitable promoters include oxides of metals from Groups IIA, IIIB, IVB, VB, VIIB and/or VIIB of the Periodic Table, oxides of the lanthanides and/or the actinides. Preferably, the catalyst comprises at least one of an element in Group IVB, VB and/or VIIB of the Periodic Table, in particular titanium, zirconium, manganese and/or vanadium. As an alternative or in addition to the metal oxide promoter, the catalyst may comprise a metal promoter selected from Groups VIIB and/or VIII of the Periodic Table. Preferred metal promoters include rhenium, platinum and palladium.

A most suitable catalyst comprises iron as this catalyst is suited for the lower hydrogen to carbon monoxide ratio as typically obtained in step (a). However by performing the process according to the present invention it also becomes possible to use cobalt based Fischer-Tropsch catalyst, which require a higher hydrogen to carbon monoxide ratio. A most suitable catalyst comprises cobalt as the catalytically active metal and zirconium as a promoter. Another most suitable catalyst comprises cobalt as the catalytically active metal and manganese and/or vanadium as a promoter.

The promoter, if present in the catalyst, is typically present in an amount of from 0.1 to 60 parts by weight per 100 parts by weight of carrier material. It will however be appreciated that the optimum amount of promoter may vary for the respective elements which act as promoter. If the catalyst comprises cobalt as the catalytically active metal and manganese and/or vanadium as promoter, the cobalt:(manganese+ vanadium) atomic ratio is advantageously at least 12:1.

The Fischer-Tropsch synthesis is preferably carried out at a temperature in the range from 125 to 350° C., more preferably 175 to 275° C., most preferably 200 to 260° C. The pressure preferably ranges from 5 to 150 bar abs., more preferably from 5 to 80 bar abs.

Hydrogen and carbon monoxide (synthesis gas) is typically fed to the three-phase slurry reactor at a molar ratio in the range from 0.4 to 2.5. Preferably, the hydrogen to carbon monoxide molar ration is in the range from 1.0 to 2.5.

The gaseous hourly space velocity may very within wide ranges and is typically in the range from 1500 to 10000 Nl/l/h, preferably in the range from 2500 to 7500 Nl/l/h.

The Fischer-Tropsch synthesis is preferably carried out in multi-tubular reactor, or in a slurry phase regime, or an ebullating bed regime wherein the catalyst particles are kept in suspension by an upward superficial gas and/or liquid velocity.

It will be understood that the skilled person is capable to select the most appropriate conditions for a specific reactor configuration and reaction regime.

Preferably, the superficial gas velocity of the synthesis gas is in the range from 0.5 to 50 cm/sec, more preferably in the range from 5 to 35 cm/sec.

Typically, the superficial liquid velocity is kept in the range from 0.001 to 4.00 cm/sec, including liquid production. It will be appreciated that he preferred range may depend on the preferred mode of operation.

Step (c)

In step (c) at least a part of the off-gas from the Fischer-Tropsch reaction is subjected to hydrogenation. This is performed using a steam/off-gas mol ratio in the range of between 0.5 and 1.5, preferably between 0.7 and 1.5, more preferably between 0.8 and 1.2, and a catalyst comprising copper and zinc or a catalyst comprising copper, zinc and manganese.

In step (c) olefins and/or paraffins are hydrogenated. Additionally at least a part of the carbon monoxide in the off-gas is converted to carbon dioxide by reaction with water. This is also referred to as shift reaction, or as water gas shift reaction.

Step (c) may be a single hydrogenation step or two or more hydrogenation steps. When step (c) comprises two or more hydrogenation steps different catalysts may be used in the different hydrogenation steps.

Hydrogenation step (c) is very useful. For example, when an adiabatic steam reformer (ASR) is used for step (e) the temperature of the feed to the ASR is usually rather high (inlet temperature of around 500° C.) in order to compensate for the low activity of the catalysts used therein. At such temperatures, the presence of CO in the inlet end of the hydrogen manufacturing unit causes coking according to the Boudouard reaction below (1).

$$2CO \rightarrow C + CO_2 \qquad (1)$$

Similarly, when an SMR is used as hydrogen manufacturing unit for step (e), the presence of CO at the inlet may cause that coke is formed at the inlet of the SMR.

Olefins and paraffins are also known for causing coking of catalyst(s) in the hydrogen manufacturing unit that is used in step (e). Carbon deposition or coking leads to hot spots on the catalyst and consequently reduces their activity. The hot spots are also formed on the reformer reactor tubes, and reduce their lifetime. The carbon deposits can be avoided or mitigated if olefins and preferably CO are removed from the off-gas stream.

Preferably a portion of at least the olefins within an off-gas stream is removed or converted before using the off-gas as a feed in step (e). In addition, the reaction preferably converts the carbon monoxide into methane and/or carbon dioxide, especially by reaction with water under the formation of carbon dioxide and hydrogen.

Preferably also other compounds are removed from the off-gas stream which can result in carbon deposition, for example CO, paraffins heavier than LPG and light naphtha. Thus preferably a portion of the olefins present in said off-gas are hydrogenated. More preferably the carbon monoxide present in said off-gas is removed or converted either prior to, simultaneous with or after the olefin hydrogenation step.

Typically the carbon monoxide is converted to a species which is not liable to cause carbon deposition, for example carbon dioxide or methane. The carbon monoxide is preferably not converted to a species which is liable to cause carbon deposition, such as carbon. Preferably a catalyst is used which combines olefin hydrogenation activity and CO shift activity. In that way olefins and carbon monoxide are removed, while additional hydrogen is made.

Suitable catalysts for step (c) are catalysts comprising copper and zinc, or copper, zinc and manganese.

Before use the catalyst may comprise copper oxide. Such a catalyst may be activated by a reduction process to obtain metallic copper. Preferably the activated catalyst to be used in step (c) comprises metallic copper on a bulk of zinc, which may comprise metallic zinc and/or zinc oxide. Additionally or alternatively, catalysts comprising copper, zinc and manganese may be used.

Hydrogenation step (c) may be performed in a single reactor. Preferably the hydrogenation step (c) is achieved in at least two reactors.

In case two reactors comprising copper are used for step (c), the second reactor for step (c) preferably is provided in parallel with the first reactor for step (c). This provides the option to reload one reactor without stopping the operation of the other reactor for step (c). Sometimes this is referred to as a lead/lag configuration.

Steam is added to the reactor(s) for step (c). Hydrogenation is achieved using a steam/off-gas mol ratio in the range of between 0.7 and 1.5 and a catalyst comprising copper and zinc or a catalyst comprising copper, zinc and manganese in the one or more reactors for step (c). The inlet temperature used for a reactor used for hydrogenation step (c) preferably is in the range of between 200 and 300° C., more preferably between 220 and 270° C.

Step (d)

In step (d) at least a part of the gas resulting from step (c) is subjected to conversion using a nickel based catalyst. In step (d) carbon monoxide is converted to carbon dioxide and/or to methane. The conversion to carbon dioxide may be a water gas shift reaction. The conversion to methane is also referred to as methanation. Other reactions that may take place during step (d) are the conversion of hydrocarbons to syngas and/or hydrogenation of olefins.

The nickel based catalyst comprises at most 0.2 wt % cobalt, at most 0.2 wt % iron and at most 0.2 wt % ruthenium, calculated on the total weight of the catalyst. The nickel based catalyst preferably comprises at most 0.1 wt % cobalt, at most 0.1 wt % iron and at most 0.1 wt % ruthenium, calculated on the total weight of the catalyst. The nickel based catalyst more preferably comprises at most 0.05 wt % cobalt, at most 0.05 wt % iron and at most 0.05 wt % ruthenium, calculated on the total weight of the catalyst. Even more preferably the nickel based catalyst does not comprise cobalt, iron or ruthenium. Cobalt, iron and ruthenium may cause a Fischer-Tropsch reaction during conversion step (d) in addition to the conversion of carbon monoxide to carbon dioxide and/or methane. This could result in blocking of the active sites of the nickel based catalyst by wax.

A suitable catalyst for step (d) comprises nickel on an alumina support. Such a catalyst is also referred to as a pre-reforming catalyst.

A suitable catalyst for step (d) comprises 5-60 wt % NiO, calculated on the total weight of the catalyst. The catalyst may comprise a promoter. Suitable promoters are chromium, zirconium, calcium and lanthanum. Preferably calcium and/or lanthanum is/are used as promoter(s).

The support of the nickel based catalyst preferably is a ceramic support. More preferably the support comprises alumina ($Al_2O_3$), silica ($SiO_2$), calcium aluminate ($CaO/Al_2O_3$), or mixtures thereof. The support may also comprise calcium, alumina and potassium oxide.

The inlet temperature used for a reactor used for step (d) preferably is in the range of between 300 and 500° C., more preferably between 350 and 500° C., even more preferably between 350 and 400° C.

In step (d) steam is preferably used in a steam/dry gas molar ratio of 0.5 to 1.5, preferably between 0.7 and 1.5, more preferably between 0.8 and 1.2. As steam is added to step (c) of the process of the invention it may not be necessary to add any steam to step (d) to arrive at a steam/dry gas molar ratio of 0.5 to 1.5 in step (d).

Step (e)

In step (e) a hydrogen comprising gas is prepared from at least a part of the gas resulting from step (d).

Step (e) may be any process, which can prepare a hydrogen comprising mixture. The process (e) may be performed in a hydrogen manufacturing unit.

Step (e) preferably is performed using a reforming process, more preferably using a steam reforming process. Even more preferably a steam methane reforming process (SMR), an adiabatic steam reforming process (ASR), a fired steam reforming process, or an auto thermal steam reforming process (ATR) is used. Most preferably an adiabatic steam reforming process (ASR) or a steam methane reforming process (SMR) is used.

In case the carbonaceous feedstock used in step (a) is coal, the process used in step (e) preferably is adiabatic steam reforming. In case the carbonaceous feedstock used in step (a) is natural gas, the process used in step (e) preferably is a steam methane reforming.

Step (e) and step (a) are separate steps resulting in separate gaseous products. The gaseous products as separately obtained may be combined after performing the separate steps.

Prior to performing step (e) olefins and/or paraffins present in the off-gas are hydrogenated, and carbon monoxide is converted to carbon dioxide and/or methane. This is performed in steps (c) and (d).

Nevertheless, the hydrogen comprising gas prepared in step (e) may comprise carbon monoxide. Usually the $H_2/CO$ ratio of the hydrogen comprising gas is 4:1 to 9:1.

Preferably a portion or all of the hydrogen comprising gas prepared in step (e) is used as a part of the hydrogen/carbon monoxide mixture feed in step (b). This may be effected by blending the hydrogen comprising gas produced in step (e) with the mixture as obtained in step (a), or by directly feeding the hydrogen comprising gas obtained in step (e) to step (b). The purity of the hydrogen comprising gas obtained in step (e) may be increased by known processes such as membrane separation, pressure swing absorbers (PSA) or combinations of a membrane unit followed by a PSA.

A portion of the optionally further purified hydrogen comprising mixture, particularly the hydrogen, as obtained in step (e) is preferably used to upgrade the paraffin product as obtained in step (b). More preferably said upgrading comprises hydrogenation, hydroisomerisation and/or hydrocracking, hydrodesulphurisation and catalytic dewaxing. Such upgrading processes as for example illustrated in WO02070629A1 in the context of a Fischer-Tropsch process.

If one requires even more hydrogen it is preferred to also use an additional hydrocarbon feedstock as feedstock in step (e). Such an additional hydrocarbon feedstock may be a methane comprising gas, LPG and naphtha. The LPG and naphtha may be derived from a mineral source or may be the LPG and/or naphtha products as isolated and obtained from the paraffin product as obtained in step (b) of the process of the present invention. Examples of methane comprising gasses may be refinery off-gas, coal bed methane or natural gas. Coal bed methane is preferred when the solid carbonaceous feedstock is coal because the coal bed methane is often found in the same location as the coal. The additional methane comprising gas may be subjected to the same hydrogenation type steps as described above if the gas comprises similar components, which require removal prior to feeding the gas to step (e).

Hydrocarbon Removal

After step (b) and before step (c) of the process of the present invention, hydrocarbons may be removed from the off-gas from the Fischer-Tropsch reaction. This may be performed in process step (bI).

The present invention thus also relates to a process for preparing a paraffin product from a carbonaceous feedstock comprising the following successive steps, (a) partial oxidation of the carbonaceous feedstock to obtain a mixture comprising hydrogen and carbon monoxide, (b) performing a Fischer-Tropsch reaction using the mixture as obtained in step (a) and recovering an off-gas from the Fischer-Tropsch reaction and a paraffin product, (bI) removing hydrocarbons from at least a part of the off-gas from the Fischer-Tropsch reaction, (c) subjecting at least a part of the gas resulting from step (bI) to hydrogenation using a steam/off-gas mol ratio in the range of between 0.5 and 1.5, preferably between 0.7 and 1.5, and a catalyst comprising copper and zinc or a catalyst comprising copper, zinc and manganese, (d) subjecting at least a part of the gas resulting from step (c) to conversion using a nickel based catalyst which comprises at most 0.2 wt % cobalt, at most 0.2 wt % iron and at most 0.2 wt % ruthenium, calculated on the total weight of the catalyst, and (e) preparing a hydrogen comprising gas from at least a part of the gas resulting from step (d), preferably using a reforming process, more preferably using a steam reforming process, even more preferably using a steam methane reforming process, an adiabatic steam reforming process, a fired steam reforming process, or an auto thermal steam reforming process, most preferably using an adiabatic steam reforming process or a steam methane reforming process.

In step (bI) hydrocarbons are removed from at least a part of the off-gas from the Fischer-Tropsch reaction. The Fischer-Tropsch off-gas comprises hydrogen, carbon monoxide, carbon dioxide, nitrogen, and C3+ hydrocarbons.

Step (bI) may be performed by:

I) contacting at least a part of the off-gas from the Fischer-Tropsch reaction, which comprises hydrogen, carbon monoxide, carbon dioxide, nitrogen, and $C_3+$ hydrocarbons, optionally after cooling, with a wash fluid in a scrubber;

II) removing wash fluid and at least a portion of the $C_3+$ hydrocarbons in a stream from the scrubber of step I);
III) removing the remaining off-gas in a separate stream from the scrubber of step I);
IV) providing a feed comprising at least a part of the stream obtained in step II) to a separator;
V) separating at least a part of the stream obtained in step II) in the separator of step IV) into at least one light stream and one heavy stream, said light stream preferably comprising carbon monoxide and carbon dioxide and said heavy stream preferably comprising hydrocarbons with at least 3 carbon atoms;
VI) splitting at least a part of the heavy stream obtained in step V) into at least two streams, whereby at least one stream comprises wash fluid and another stream comprises hydrocarbons with at least 3 carbon atoms and at most 5 vol % of hydrocarbons with 10 or more carbon atoms;
VII) providing a feed comprising at least a part of the wash fluid comprising stream obtained in step VI) to the scrubber of step I);
VIII) optionally providing a further feed comprising wash fluid to the scrubber of step I).

Preferably all steps of step (bI) are performed in the order of numbering. The process may comprise additional steps.

The heavy stream preferably comprising hydrocarbons with at least 3 carbon atoms that is separated in step V) contains the hydrocarbons that are removed from the off-gas in step (bI).

The light stream preferably comprising carbon monoxide and carbon dioxide which is separated in step V) is subjected to hydrogenation in step (c).

The present invention thus also relates to a process for preparing a paraffin product from a carbonaceous feedstock comprising the following successive steps,
(a) partial oxidation of the carbonaceous feedstock to obtain a mixture comprising hydrogen and carbon monoxide,
(b) performing a Fischer-Tropsch reaction using the mixture as obtained in step (a) and recovering an off-gas from the Fischer-Tropsch reaction and a paraffin product, (bI) removing hydrocarbons from at least a part of the off-gas from the Fischer-Tropsch reaction by:
  I) contacting at least a part of the off-gas from the Fischer-Tropsch reaction, which comprises hydrogen, carbon monoxide, carbon dioxide, nitrogen, and C3+ hydrocarbons, optionally after cooling, with a wash fluid in a scrubber;
  II) removing wash fluid and at least a portion of the C3+ hydrocarbons in a stream from the scrubber of step I);
  III) removing the remaining off-gas in a separate stream from the scrubber of step I);
  IV) providing a feed comprising at least a part of the stream obtained in step II) to a separator;
  V) separating at least a part of the stream obtained in step II) in the separator of step IV) into at least one light stream and one heavy stream, said light stream preferably comprising carbon monoxide and carbon dioxide and said heavy stream preferably comprising hydrocarbons with at least 3 carbon atoms;
  VI) splitting at least a part of the heavy stream obtained in step V) into at least two streams, whereby at least one stream comprises wash fluid and another stream comprises hydrocarbons with at least 3 carbon atoms and at most 5 vol % of hydrocarbons with 10 or more carbon atoms;
  VII) providing a feed comprising at least a part of the wash fluid comprising stream obtained in step VI) to the scrubber of step I);
  VIII) optionally providing a further feed comprising wash fluid to the scrubber of step I);
(c) subjecting the light stream preferably comprising carbon monoxide and carbon dioxide which is separated in step V) to hydrogenation using a steam/off-gas mol ratio in the range of between 0.5 and 1.5, preferably between 0.7 and 1.5, and a catalyst comprising copper and zinc or a catalyst comprising copper, zinc and manganese,
(d) subjecting at least a part of the gas resulting from step (c) to conversion using a nickel based catalyst which comprises at most 0.2 wt % cobalt, at most 0.2 wt % iron and at most 0.2 wt % ruthenium, calculated on the total weight of the catalyst, and
(e) preparing a hydrogen comprising gas from at least a part of the gas resulting from step (d), preferably using a reforming process, more preferably using a steam reforming process, even more preferably using a steam methane reforming process, an adiabatic steam reforming process, a fired steam reforming process, or an auto thermal steam reforming process, most preferably using an adiabatic steam reforming process or a steam methane reforming process.

Steps V) and VI) are performed in different units. Separating step V) is performed in a separating unit. Splitting step VI) is performed in a splitting unit. Splitting step VI) preferably results in two streams.

In step I) at least a part of the off-gas from the Fischer-Tropsch reaction, which comprises hydrogen, carbon monoxide, carbon dioxide, nitrogen, and $C_3+$ hydrocarbons, is contacted with a wash fluid in a scrubber.

Preferably the off-gas from the Fischer-Tropsch reaction is cooled in one or more stages before step I). During the cooling step(s) hydrocarbon product, especially $C_5+$ hydrocarbons, and/or water may be separated from the off-gas. Before cooling, the temperature of the off-gas may be 180-280° C., preferably 210-260° C. After cooling the off-gas preferably is at a temperature of 50° C. or lower.

In one embodiment, the off-gas is first cooled by 50-200° C., preferably 80-100° C. In this first cooling step the off-gas preferably is cooled to 100-160° C., more preferably to 120-140° C. Then the off-gas is cooled even further in a second cooling step in which the off-gas is cooled by 20-130° C., preferably 50-90° C. In this embodiment the off-gas is optionally subjected to a third cooling step.

Step (bI) particularly aims at the removal of C3+ hydrocarbons from Fischer-Tropsch off-gas comprising hydrogen, carbon monoxide, carbon dioxide, nitrogen, and $C_3+$ hydrocarbons. The off-gas may additionally comprise other components such as methane, hydrocarbons comprising 2 carbon atoms, water, and/or argon. The off-gas may comprise oxygenates, also referred to as oxygenated compounds, such as methanol and dimethyl ether. In case the off-gas comprises $C_3+$ oxygenates, $C_3+$ oxygenates may also be removed in step (bI).

The off-gas that is contacted with the wash fluid in step I) preferably is in a gaseous state at a pressure between 1 and 80 bar, preferably between 20 and 70 bar, and a temperature above 0° C. and below 50° C., preferably a temperature above 10° C. and below 40° C. Preferably at least 90 volume %, more preferably at least 95 volume %, even more preferably at least 99 volume % of the hydrocarbons in the off-gas that is contacted with the wash fluid in step I) consists of hydrocarbons comprising 3 to 9 carbon atoms, hydrocarbons comprising 2 carbon atoms, and methane. Preferably at least 0.005 volume %, more preferably at least 0.01 volume %, even more preferably at least 0.1 volume %, still more preferably at least 1 volume % of the hydrocarbons in the off-gas that is contacted with the wash fluid in step I) consists of hydrocarbons comprising 3 to 9 carbon atoms.

The wash fluid used in step I) comprises hydrocarbons. Preferably at least 60 weight %, more preferably at least 70 weight %, even more preferably at least 80 weight % of the hydrocarbons in the wash fluid consists of $C_5$-$C_{20}$ hydrocarbons, preferably $C_8$-$C_{20}$ hydrocarbons, more preferably $C_8$-$C_{14}$ hydrocarbons.

The wash fluid used in step I) preferably is kerosene, more preferably kerosene comprising at least 80 weight % $C_6$-$C_{16}$ hydrocarbons, even more preferably kerosene comprising at least 80 weight % $C_8$-$C_{16}$ hydrocarbons, still more preferably kerosene comprising at least 80 weight % $C_8$-$C_{14}$ hydrocarbons or $C_{10}$-$C_{14}$ hydrocarbons.

In one embodiment, the wash fluid used in step I) comprises at least 80 weight % $C_6$-$C_{16}$ hydrocarbons, more preferably at least 80 weight % $C_8$-$C_{16}$ hydrocarbons, even more preferably comprises at least 80 weight % $C_8$-$C_{14}$ hydrocarbons or at least 80 weight % $C_{10}$-$C_{14}$ hydrocarbons. This wash fluid may optionally be hydrogenated before it is used as wash fluid.

In another embodiment, the wash fluid used in step I) is light detergent feedstock (LDF), even more preferably LDF comprising at least 80 weight % $C_{10}$-$C_{14}$ hydrocarbons, still more preferably LDF comprising at least 80 weight % $C_{10}$-$C_{13}$ hydrocarbons.

The wash fluid used in step I) preferably is kerosene, more preferably kerosene comprising at least 80 weight % $C_6$-$C_{16}$ hydrocarbons, even more preferably kerosene comprising at least 80 weight % $C_8$-$C_{16}$ hydrocarbons, still more preferably kerosene comprising at least 80 weight % $C_8$-$C_{14}$ hydrocarbons.

Preferably the initial boiling point of the wash fluid is higher than 80° C., more preferably higher than 100° C. The higher the initial boiling point of the wash fluid the easier it is to separate C3+ hydrocarbons from the wash fluid.

The Fischer-Tropsch off-gas preferably is at a temperature of 0-50° C., preferably 10-40° C. when it enters the scrubber. Preferably the pressure of the Fischer-Tropsch off-gas is 1-80 bar, preferably 20-70 bar, when it enters the scrubber. Preferably the scrubber is adapted to provide maximum contact between the off-gas and the wash fluid with minimum pressure drop. Preferably the pressure during the contacting step is the same as the off-gas pressure.

In step II) wash fluid and at least a portion of the $C_3$+ hydrocarbons are removed in a stream from the scrubber of step I). Step (bI) proofed to be very effective in removing $C_3$+ hydrocarbons from the off-gas.

After removal of at least a portion of the $C_3$+ hydrocarbons from the off-gas by means of the wash fluid, the remaining off-gas is removed in a separate stream from the scrubber of step I). This is performed in step III). The removal of the remaining off-gas may, for example, be performed when regenerating the scrubber of step I). The stream comprising the remaining off-gas may be used for the production of electrical power, in an expanding/combustion process such as in a gas turbine, as burner fuel, or it may be fed to a syngas production process. The energy generated in the process may be used for own use or for export to local customers. Part of the energy could be used for the compression of an oxygen containing gas.

In step IV) at least a part of the stream obtained in step II) is fed to a separator.

In step V) separation takes place in the separator of step IV). The separator comprises at least a part of the stream obtained in step II), and optionally other materials. The separation results in at least one light stream and one heavy stream, whereby said light stream preferably comprises carbon monoxide and carbon dioxide and said heavy stream preferably comprises hydrocarbons with at least 3 carbon atoms.

The light stream obtained in step V) more preferably comprises carbon monoxide, carbon dioxide, methane, and hydrocarbons containing 2 carbon atoms, and optionally oxygenates comprising 2 carbon atoms. The heavy stream obtained in step V) comprises $C_3$+ hydrocarbons resulting from the stream obtained in step II).

The separator(s) used in step V) may be a stripper, for example a light ends stripper, a flasher, and/or a distillation unit, or any other suitable separation unit. Preferably the separator or one of the separators, used in step V) is a stripper, more preferably a light ends stripper.

The separation(s) in step V) preferably take(s) place at a pressure in the range of from 1 to 20 bar, more preferably 1 to 5 bar, even more preferably at about 1 bar.

In step VI) splitting is performed in a splitting unit. Splitting step VI) preferably results in two streams. The splitting unit used in step VI) may be a splitter, stripper, a flasher, and/or a distillation unit, or any other suitable separation unit. Preferably a splitter is used in step VI).

In step VII) a feed comprising at least a part of the wash fluid comprising stream obtained in step VI) is provided to the scrubber of step I). A further feed comprising wash fluid may be provided to the scrubber of step I) in optional step VIII). Such a further feed comprising wash fluid may be a make up stream. During the process it may be desired to add some extra wash fluid, and this may be performed by providing a further feed comprising wash fluid to the scrubber of step I).

In case the wash fluid is kerosene, the further feed that may be added in step VIII) preferably is kerosene. In case the wash fluid is LDF, the further feed that may be added in step VIII) preferably is LDF.

Optionally a part of the stream comprising hydrocarbons with at least 3 carbon atoms, and at most 5 vol % of hydrocarbons with 10 or more carbon atoms, obtained in step VI) is subjected to hydrogenation to obtain one or more products such as LPG.

Experiments have been performed at optimal process conditions for hydrogenation step (c).

EXAMPLE 1

The off-gas from the Fischer-Tropsch reaction comprised 12.2 vol % CO, 23.9 vol % $CO_2$, 6.5 vol % $H_2$, 25.4 vol % $N_2$, 30.5 vol % $CH_4$, and 1.1 vol % $C_2H_4$.

Steam was added to this dry gas. The steam/off-gas molar ratio was 1.2. Hydrogenation step (c) was performed using a catalyst comprising copper and zinc. The temperature at the inlet of the reactor was 220° C. The pressure was 400 psig.

The very stable catalyst performance of the hydrogenation catalyst under these conditions is shown in Table 1.

TABLE 1

| | | Outlet Time on stream (hrs) | |
|---|---|---|---|
| Composition | Inlet | 40 | 64 |
| N2 (vol. %) | 25.35 | 22.59 | 22.62 |
| CO (vol. %) | 12.25 | 0.29 | 0.30 |
| CH4 (vol. %) | 30.47 | 27.51 | 27.50 |
| CO2 (vol. %) | 23.94 | 31.98 | 32.07 |
| H2 (vol. %) | 6.48 | 15.83 | 15.82 |

TABLE 1-continued

| Composition | Inlet | Outlet Time on stream (hrs) | |
|---|---|---|---|
| | | 40 | 64 |
| C2H4 (vol. %) | 1.14 | 0.01 | 0.01 |
| C2H6 (vol. %) | 0.00 | 1.03 | 1.03 |

EXAMPLE 2

The off-gas from the Fischer-Tropsch reaction comprised 12.7 vol % CO, 25.4 vol % $CO_2$, 6.8 vol % $H_2$, 25.3 vol % $N_2$, 28.8 vol % $CH_4$, and 0.97 vol % $C_2H_4$.

Steam was added to this dry gas. The steam/off-gas molar ratio was 0.8. Hydrogenation step (c) was performed using a catalyst comprising copper, zinc and manganese. An isothermal reactor was used. The temperature at the inlet and at the outlet of the reactor was 250° C. The pressure was 400 psig. The extremely stable catalyst performance of the hydrogenation catalyst under these conditions is shown in Table 2.

TABLE 2

| Composition | Inlet | Outlet Time on stream (hrs) 360 |
|---|---|---|
| N2 (vol. %) | 25.3 | 22.5 |
| CO (vol. %) | 12.7 | 0.115 |
| CH4 (vol. %) | 28.8 | 25.9 |
| CO2 (vol. %) | 25.4 | 34 |
| H2 (vol. %) | 6.85 | 16.6 |
| C2H4 (vol. %) | 0.968 | 0 |
| C2H6 (vol. %) | 0.00 | 0.965 |

In Example 2, the CO conversion was 99%, which was stable during the entire duration of the test (360 hours). The ethylene conversion was 100%, which was stable during the entire duration of the test (360 hours).

EXAMPLE 3

The off-gas from the Fischer-Tropsch reaction comprised 20.0 vol % CO, 27.4 vol % $CO_2$, 11.25 vol % $H_2$, 6.6 vol % $N_2$, 31.75 vol % $CH_4$, and 1 vol % $C_2H_4$.

Steam was added to this dry gas. The steam/off-gas molar ratio was 1.2. Hydrogenation step (c) was performed using two reactors in parallel and using in both reactors a catalyst tablets with a height of 4.5 mm and a diameter of 4.5 mm which comprised copper, zinc and manganese. There were temperature cycles from 250° C. to 330° C. for both reactors. The pressure in both reactors was 400 psig.

Both reactors had the same feed, but at another gas space velocity. The dry gas space velocity was 2500 $Nm^3/m^3$ of loaded catalyst/hour for the first reactor, and 5000 $Nm^3/m^3$ of loaded catalyst/hour for the second reactor.

An extremely stable catalyst performance of the hydrogenation catalyst under these conditions was found.

In Example 3, at a reactor temperature of 300° C., the CO conversion in the first reactor was 98.5%, which was stable during the entire duration of the test (384 hours). The ethylene conversion in the first reactor was 100%, which was stable during the entire duration of the test (384 hours).

In Example 3, at a reactor temperature of 300° C., the CO conversion in the second reactor was 98.1%, which was stable during the entire duration of the test (384 hours). The ethylene conversion in the second reactor was 99.87%, which was stable during the entire duration of the test (384 hours).

EXAMPLE 4

The off-gas from the Fischer-Tropsch reaction comprised 12.6-13.1 vol % CO, 37.1-38.0 vol % $CO_2$, 6.7-9.3 vol % $H_2$, 6.1-6.8 vol % $N_2$, 33.3-34.5 vol % $CH_4$, and 2 vol % $C_2H_4$.

Steam was added to this dry gas. The steam/off-gas molar ratio was 0.6. Hydrogenation step (c) was performed using catalyst tablets with a height of 4.5 mm and a diameter of 4.5 mm which comprised copper, zinc and manganese. The temperature at the inlet of the reactor was 200° C. and the temperature at the outlet of the reactor was 320° C. The pressure was 30 bar. The dry gas space velocity was 4000 $Nm^3/m^3$ of loaded catalyst/hour.

An extremely stable catalyst performance of the hydrogenation catalyst under these relatively severe conditions was found. After 483 hours only a small deactivation of the catalyst was observed. The initial ethylene conversion was 100% and dropped to 97%; the initial CO conversion was 95% and dropped to 92%.

CONCLUSION

From the examples follows that a catalyst comprising copper and zinc or a catalyst comprising copper, zinc and manganese can be used very well to hydrogenate olefins in Fischer-Tropsch off-gas, and to convert most of the carbon monoxide in the off-gas in a shift reaction, when a steam/off-gas mol ratio in the range of between 0.5 and 1.5 is used. The catalyst life time of the hydrogenation catalyst has been increased significantly.

The remaining olefins can be hydrogenated and the remaining carbon monoxide can be converted to carbon dioxide and/or to methane using a nickel based catalyst. This is very well possible as the gas comprises hardly any oxygenates after treatment with the Cu/Zn or the Cu/Zn/Mn catalyst at a steam/off-gas mol ratio in the range of between 0.5 and 1.5.

After treatment with the nickel base catalyst the resulting gas has such a low level of olefins and of carbon monoxide that it is highly suitable to be processed in a reforming process to prepare a hydrogen comprising gas. The resulting gas can, for example, be fed to the process-side of an SMR whereby the remaining low carbon monoxide level will not cause any problems.

The invention claimed is:

1. A method for preparing a paraffin product from a carbonaceous feedstock comprising the following steps:
   (a) partial oxidation of the carbonaceous feedstock to obtain a mixture comprising hydrogen and carbon monoxide;
   (b) performing a Fischer-Tropsch reaction using the mixture as obtained in step (a) and recovering an off-gas from the Fischer-Tropsch reaction and a paraffin product;
   (c) subjecting at least a part of the off-gas from the Fischer-Tropsch reaction to conversion of carbon monoxide to carbon dioxide and to hydrogenation using a steam/off-gas mol ratio in the range of between 0.5 and 1.5, and a catalyst comprising copper and zinc;
   (d) subjecting at least a part of the gas resulting from step (c) to conversion using a nickel based catalyst comprising at most 0.2 wt % cobalt, at most 0.2 wt % iron and at most 0.2 wt % ruthenium, calculated on the total weight of the catalyst; and,
(e) preparing a hydrogen comprising gas from at least a part of the gas resulting from step (d) using a reforming process.

2. The method of claim 1, wherein the steam/off-gas mol ratio in step (c) is in the range of between 0.7 and 1.5.

3. The method of claim 1, wherein the steam/off-gas mol ratio in step (c) is in the range of between 0.8 and 1.2.

4. The method of claim 1, wherein the reforming comprises a process selected from the group consisting of: a steam reforming process, a steam methane reforming process, an adiabatic steam reforming process, a fired steam reforming process, an auto thermal steam reforming process, and an adiabatic steam reforming process.

5. The method of claim 1, wherein the inlet temperature used for a reactor used for conversion and hydrogenation step (c) is in the range of between 200 and 300° C.

6. The method of claim 1, wherein conversion and hydrogenation step (c) is performed using two or more reactors in parallel.

7. The method of claim 1, wherein the inlet temperature used for a reactor used for step (d) is in the range of between 300 and 500° C.

8. The method of claim 1, wherein the steam/off-gas mol ratio used for step (c) is in the range of between 0.8 and 1.2.

9. The method of claim 1, wherein after step (b) and before step (c) hydrocarbons are removed from the off-gas from the Fischer-Tropsch reaction.

10. The method of claim 9 wherein the hydrocarbons are removed from the off-gas from the Fischer-Tropsch reaction by:

I) contacting at least a part of the off-gas from the Fischer-Tropsch reaction with a wash fluid in a scrubber;

II) removing wash fluid and at least a portion of the C3+ hydrocarbons in a stream from the scrubber of step I);

III) removing the remaining off-gas in a separate stream from the scrubber of step I);

IV) providing a feed comprising at least a part of the stream obtained in step II) to a separator;

V) separating at least a part of the stream obtained in step II) in the separator of step IV) into at least one light stream and one heavy stream, said light stream preferably comprising carbon monoxide and carbon dioxide and said heavy stream preferably comprising hydrocarbons with at least 3 carbon atoms;

VI) splitting at least a part of the heavy stream obtained in step V) into at least two streams, whereby at least one stream comprises wash fluid and another stream comprises hydrocarbons with at least 3 carbon atoms and at most 5 vol % of hydrocarbons with 10 or more carbon atoms;

VII) providing a feed comprising at least a part of the wash fluid comprising stream obtained in step VI) to the scrubber of step I).

11. The method of claim 10 further comprising:

VIII) providing a further feed comprising wash fluid to the scrubber of step I), and whereby the light stream preferably comprising carbon monoxide and carbon dioxide which is separated in step V) is subjected to hydrogenation in step (c).

* * * * *